United States Patent [19]

Jamas et al.

[11] Patent Number: 5,032,401
[45] Date of Patent: Jul. 16, 1991

[54] GLUCAN DRUG DELIVERY SYSTEM AND ADJUVANT

[75] Inventors: Spiros Jamas, Boston; Gary R. Ostroff, Worcester; D. Davidson Easson, Jr., Shrewsbury, all of Mass.

[73] Assignee: Alpha Beta Technology, Worcester, Mass.

[21] Appl. No.: 366,490

[22] Filed: Jun. 15, 1989

[51] Int. Cl.$^5$ .................... A61K 39/00; A61K 39/12; A61K 39/36; A61K 31/715
[52] U.S. Cl. ...................... 424/426; 424/88; 424/89; 424/92; 514/54; 514/885; 530/817
[58] Field of Search ............... 424/426, 88, 89, 91, 424/92; 514/54; 530/812, 813, 817

[56] References Cited

U.S. PATENT DOCUMENTS

| | | | |
|---|---|---|---|
| 4,705,780 | 11/1987 | Massot et al. | 514/54 |
| 4,739,046 | 4/1988 | DiLuzio | 536/117 |
| 4,741,872 | 5/1988 | DeLuca et al. | 264/4.7 |
| 4,761,402 | 8/1988 | Williams et al. | 514/54 |
| 4,810,646 | 3/1989 | jamas et al. | 435/101 |
| 4,857,505 | 8/1989 | Arendt | 514/2 |

FOREIGN PATENT DOCUMENTS 0015175 9/1980 European Pat. Off. .

OTHER PUBLICATIONS

Glucan-Enhanced Immunogenicity of Killed Erythrocylic Stages of Plasmodium Benghei, Holbrook et al., Infection and Immunity, 32, 542 (1981).
Glucan-Induced Enhancement of Host Resistance to Selected Infectious Diseases, Reynolds et al., Infection and Immunity, 30, 51 (1980).
S. Jamas et al., *Biotech. and Bioeng.*, 28: 769–784 (1986).
Patent Abstracts of Japan, vol. 8, No. 270 (Dec., 1980), Masumoto.
S. Jamas et al., In: *Industrial Polysaccharides: Genetic Engineering Structure/Property Relations and Appl.*, Elserier Science Publ. B.V., Amsterdam N. C., pp. 65–69 (1987).
J. K. Czop *Pathology and Immunopathology Research*, 5: 286–296 (1986).
J. A. Cook et al., *Survey of Immunology Research*, 2: 243–245 (1983).
W. Browder, *Survey of Immunology Research*, 2: 299–301 (1983).
M. L. Patchen, *Survey Immunology Research*, 2: 237–242 (1983).
J. A. Reynolds et al., *Infection and Immunity*, 20(1): 51–57 (1980).
T. W. Holbrook et al., *Infection and Immunity*, 32(2): 542–546 (1981).
J. L. Benach et al., *Infection and Immunity*, 35(3):947–951 (1982).
E. R. Sherwood et al., *International Journal of Immunopharmacology*, 9(3):261–267 (1987).
J. A. Cook et al., *Infection and Immunity*, 37(3): 1261–1269 (1982).
T. W. Holbrook et al., *American Journal of Tropical Medical Hygiene*, 32(1):51–53 (1983).
T. W. Holbrook et al., *American Journal fo Tropical Medical Hygiene*, 30(4):762–768 (1981).
J. A. Cook et al., *Infection and Immunity*, 40)3):1038–1043 (1983).
M. A. Chirigos et al., *Cancer Research*, 38:1085–1091 (1978).

*Primary Examiner*—Thurman Page
*Assistant Examiner*—G. S. Kishorl
*Attorney, Agent, or Firm*—Hamilton, Brook, Smith & Reynolds

[57] ABSTRACT

The invention describes a whole β-glucan drug delivery vehicle that non-specifically enhances the immune response, and is safe for human use. A drug is incorporated into a whole β-glucan microparticle, and the combination is administered to an individual. The β-glucan vehicle allows sustained release of the drug component while simultaneously enhancing the effectiveness of the drug by boosting the individual's endogenous immune response.

6 Claims, 5 Drawing Sheets

GLUCAN DRUG DELIVERY SYSTEM AND ADJUVANT

BACKGROUND OF THE DISCLOSURE

Advances in biotechnology and immunology have presented new challenges for obtaining safe and effective drugs, such as vaccines. For example, new generation subunit and antiidiotype antigens yield very safe vaccines; however, these vaccines, in general, provide poor immune stimulation and prophylactic effects. Therefore, an important aspect of any new drug or vaccine formulation is a component that enhances its safety and efficacy by providing a delivery mechanism and, in the case of vaccines, by boosting the immune response to the antigen. Adjuvants can generally be categorized as components that boost the immune response, and as delivery systems that enhance antigen presentation, provide sustained release of the drug or antigen for extended periods, or target the drug or antigen to specific immune cells.

Serious drawbacks exist in many of today's adjuvants and delivery systems. Most are crude preparations of bacterial or plant origin, or oil emulsion systems, the active components and modes of action of which are unknown. In addition, these compounds are usually toxic and cannot be used safely, especially for human applications. Some preparations of the yeast cell wall component, $\beta$-glucan have been shown to provide enhanced resistance to several infectious diseases when given in conjunction with viral vaccines or killed infected cells. Reynolds et al., 1980. *Infect. Immunity*, 30:51–57; Holbrook et al., 1981, *Infect. Immunity*, 35:534–546; Benach et al., 1982, *Infect. Immunity*, 36:947–951. Some of the adverse effects of administering other $\beta$-glucan preparations are described by Williams et al. in U.S. Pat. No. 4,761,402. These effects include anaphylaxis, granuloma development, hypotension development and a high degree of acute toxicity.

SUMMARY OF THE INVENTION

The invention relates to a novel pharmaceutical composition which i: a drug delivery vehicle and which nonspecifically enhances the immune response. The composition comprises whole glucan particles and a pharmacologically active substance, such as a drug or antigen. The drug or antigen can be contained within, uniformly dispersed with, or chemically linked to the whole glucan particles.

Methods for utilizing whole glucan particles in pharmaceutical formulations which provide, in combination, (1) the prolonged release of the drug; (2) longer half-life of the drug by protecting it from proteolytic, hydrolytic and other clearance mechanisms; (3) targeted delivery of the drug to macrophages; and (4) stimulation of the immune response are also the subject of the present invention.

When the present composition is administered to an individual the entrapped drug is released through the glucan matrix into the physiological environment. Where the drug is an antigen, the $\beta$-glucan component simultaneously acts as an adjuvant to the antigen by enhancing the immune response in the individual.

Whole glucan particles are very pure preparations of $\beta$-glucan molecules which avoid many of the undesirable side effects associated with less pure preparations. Whole glucan particles retain the in vivo three-dimensional morphology of the yeast cell walls. from which they are derived. Thus, the particles are hollow, which allows the drug or antigen to be incorporated into the cavity. Whole glucan particles have a higher water-holding capacity than $\beta$-glucans prepared by other methods which disrupt the cell walls The water-holding capacity can be controlled by modifying the $\beta$-glucan structure, for example, by modifying the amount of branching.

The invention further provides a method for providing a drug or antigen to an individual while simultaneously providing an adjuvant to boost the immune response to the drug or antigen, by administering to the individual a drug contained within (e.g., encapsulated or entrapped), or uniformly dispersed in, or chemically linked to whole glucan particles. For example, a vaccine can be incorporated into a whole glucan particle, and the particle administered to an individual to protect against an infectious disease, while simultaneously boosting the individual's immune response to the vaccine.

The invention also teaches methods to incorporate drugs or antigens into the intact whole glucan particle, thus providing substantial improvements in the administration and efficacy of drug formulations.

This invention provides a safe, non-toxic vehicle for in vivo drug delivery that also enhances the immune response, enhances drug presentation in vivo and targets the drug to specific immune cells.

DETAILED DESCRIPTION OF THE INVENTION

Figure 1:
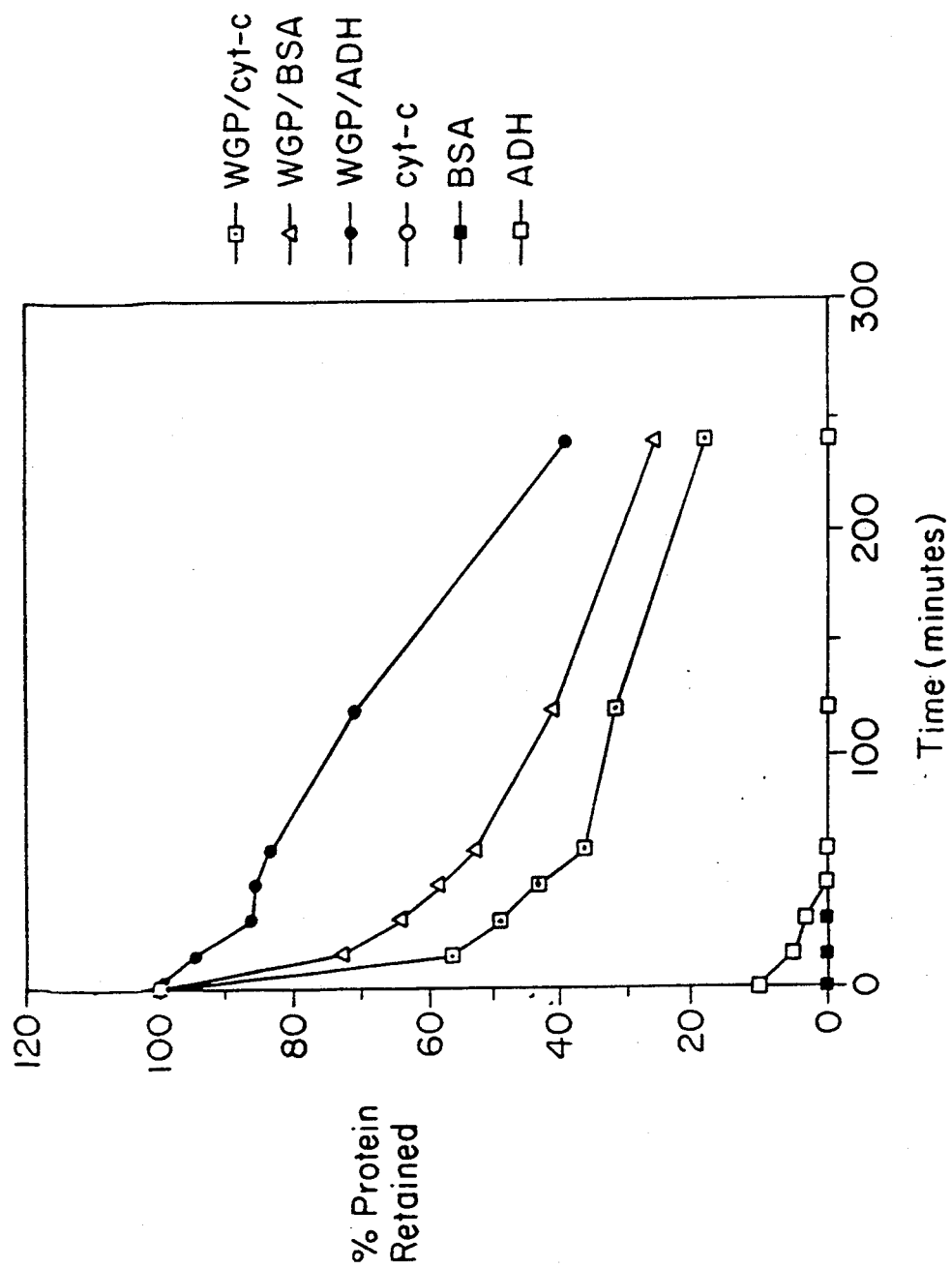
FIG. 1 is a graph illustrating the release rate of several proteins of varying molecular weight from whole glucan particles.

The invention relates to a unique pharmaceutical composition for the controlled and/or continuous release of a drug or antigen from a whole glucan particle combined with an immune system enhancement induced by the $\beta$-glucan. The composition thus provides a drug delivery and controlled release system which acts as an adjuvant to the drug. The term "adjuvant" as used herein means a substance which is added to a drug product or formulation which prolongs and enhances the action of the drug or active ingredient. For example, in a vaccine formulation, the whole glucan particles provide a vehicle which enhances antigenicity to the vaccine by prolonging its half-life, targeting it to the macrophages or antigen-presenting cells and simultaneously activating these cells.

$\beta$-Glucans provide enhanced resistance to infectious diseases by non-specifically activating a hosts' immune defense system. Activation occurs through interaction with specific β-glucan receptors on monocytes thereby inducing the release of interleukin-1 (IL-1) and other cytokines and cellular mediators. Czop, (1986) *Pathology and Immunipathology Research*, 5:286-296; Williams et al., 1988, *International Journal of Immunipharmacology*, 9:261-267.

Compositions of the present invention, comprising a whole glucan particle and a drug or other pharmacologically active substance, can be used to provide, in combination, a drug delivery vehicle, and an adjuvant in the administration of drugs or vaccines, which compositions are safe and efficacious in humans and animals. The compositions are two phase systems comprising whole glucan particles and a drug or an antigen. The compositions provide substantial improvements in the administration and efficacy of drug formulations. These improvements include include:

(1) Providing a non-toxic biodegradable carrier with a defined composition and structure;
(2) Providing a delivery vehicle capable of sustained release of the drug or antigen component;
(3) Targeting the drug or antigen component to macrophages; and
(4) Providing a non-specific immunostimulant, with a known mode of action.

This combination of properties has a synergistic effect, thus, the present invention provides a whole glucan particle delivery system that targets the drug or vaccine to macrophages, activates the macrophages, and extends the drug in vivo half-life by protecting it from degradation (proteolytic or hydrolytic) and rapid clearance, thus resulting in increased potency and efficacy compared with individual formulations of drug, antigen or whole glucan particles.

The terms "whole glucan", "whole glucan particles", "whole β-glucan" or "whole β-glucan particles" as used herein refer to whole β-glucan particles. Whole β-glucan particles are essentially micron-sized hollow spheres composed of a rigid, semi-permeable glucan matrix. Whole β-glucan particles have the ability to swell in aqueous solutions.

Whole glucan particles are prepared from yeast cells by the extraction and purification of the alkali-insoluble glucan fraction from the yeast cell walls. The yeast cells are treated with an aqueous hydroxide solution, without disrupting the yeast cell walls, which digests the protein and intracellular portion of the cell, leaving the glucan wall component devoid of significant protein contamination, and having substantially the unaltered cell wall structure of β(1-6) and β(1-3) linked glucans. A more detailed description of whole glucan particles and the process of preparing them is described by Jamas et al. in U.S. Pat. No. 4,810,646 and in co-pending patent applications U.S. Ser. No. 166,929, U.S. Ser. No. 297,752 and U.S. Ser. No. 297,982, the teachings of which are incorporated herein by reference.

Whole glucan particles have been shown to activate human monocyte macrophages by the same mechanisms characterized for other β-glucans. Czop, *Pathology and Immunopathology Research*, 5:286-296 (1986). A unique feature of the whole glucan particles is that they retain the in vivo 3-dimensional morphology of the yeast cell wall. Whole glucan particles prepared by this method have several advantages over other β-glucan preparations, such as those described by DiLuzio et al.; in the *International Journal of Cancer*, 24:773-779 and Manners et al., in *Biochemistry Journal*, 135:19-30 (1973): they are highly pure (e.g., have less than one percent (w/w) protein and less than three percent (w/w) chitin and glycogen), they are intact, having a hollow spherical shape which allows agents to be incorporated into the particles and they can be chemically modified (e.g., crosslinked) to regulate the release rate of the encapsulated drug, and the rate of degradation of the β-glucan matrix. In addition, whole glucan particles can activate macrophage cells, thus can be used as carriers or transport vehicles for administration of drugs or antigens to an individual, while simultaneously boosting the individual's immune response, thereby enhancing the action of the drug. The whole glucan carrier acts to deliver the drug or antigen directly to macrophages, where it is slowly released, causing a heightened and sustained immune response. Thus, the present composition allows drugs or antigens to be directed or targeted to macrophage cells.

The whole glucan particles are biodegradable, that is, they bioerode over time in a physiological environment. The terms "biodegradable" or "bioerodible" as used herein are defined as the property or characteristic of a body of microporous material to innocuously disintegrate or break down as a unit structure or entity over a period of time, in response to the biological environment by one or more physical or chemical degradative processes, for example by enzymatic action, hydrolysis, dissolution. The erosion rate may be controlled by varying the ratio of $β(1-6):β(1-3)$ linkages in the β-glucan matrix or by crosslinking.

The drugs suitable for use in the present composition are biologically active substances. These substances include biologically active polypeptides, antigens and vaccines. Any of the drugs used to treat the body can be incorporated in the present composition. The term "drug" is used herein in its broadest sense, as including any composition or substance that will produce a pharmacologic response. Suitable drugs for use with the composition of the invention include without limitation: protein drugs such as insulin; desensitizing agents such as antigens; vaccines such as smallpox, yellow fever, distemper, cholera, fowl pox, antivenom, scarlet fever, dyptheria toxoid, tetanus toxoid, whooping cough, influenza, rabies, mumps, measles and poliomyelitis; antibiotics, such as penicillin, tetracycline, neomycin and erythromycin; antiallergenics, steroids; decongestants; anti-cholinesterases; sedatives; tranquilizers; estrogens; humoral agents; antipsychotics; antispasmodics; antimalarials; antihistamines; cardioactive agents; nutritional agents such as vitamins, amino acids and fats. Other drugs having the same or different physiological activity as those recited above can be employed in drug delivery systems within the scope of the present invention. Suitable mixtures of drugs can also be incorporated into the composition in lieu of a single drug.

Drugs can be in various forms, such as uncharged molecules, components of molecular complexes, or pharmacologically acceptable salts, such as hydrochloride, hydrobromide, sulfate, phosphate, nitrate, borate, acetate, maleate, tartrate and salicylate. For acidic drugs, salts of metals, amines or organic cations (e.g., quaternary ammonium) can be used. Simple derivatives of the drugs (such as ethers, esters. amides), which have desirable retention and release characteristics, but which are easily hydrolyzed by body pH or enzymes can be used.

The amount of drug incorporated in the drug delivery device varies widely depending on the particular drug, the desired therapeutic effect and the time span for which it takes the glucan matrix to swell, erode or dissolve. A variety of β-glucan particles are available to provide complete dosage regimes for therapy for a range of therapeutic or prophylactic treatments, thus, there is no critical upper limit on the amount of drug incorporated into the device. The lower limit will depend upon the activity of the drug and the time span of its release from the device.

The present compositions are produced by causing the whole glucan particle to swell in the presence of a solution of the drug of choice. Various drugs can therefore be incorporated into the particles, by natural diffusion. Once absorbed within the particles these drugs may be entrapped by removing the solvent, or by precipitation (e.g., by change of pH, ionic environment or solvent). For example, proteins within the particle can be precipitated by adding ammonium sulfate, ethanol or acetone to a solution of drug and whole glucan particles. The outward diffusion or release rate of the entrapped drugs is therefore a function of their rate of dissolution in the environment of use, and their rate of diffusion through the semi-permeable glucan matrix.

Several methods can be used to swell the glucan particles. Generally, an aqueous solution of the drug to be loaded is prepared and added to an appropriate quantity of whole β-glucan particles and the mixture is allowed sufficient time (generally up to six hours) for the particles to swell. The swollen particles are then removed from the solution, and dried, or contacted with another compound to precipitate the entrapped drug.

Figure 2:
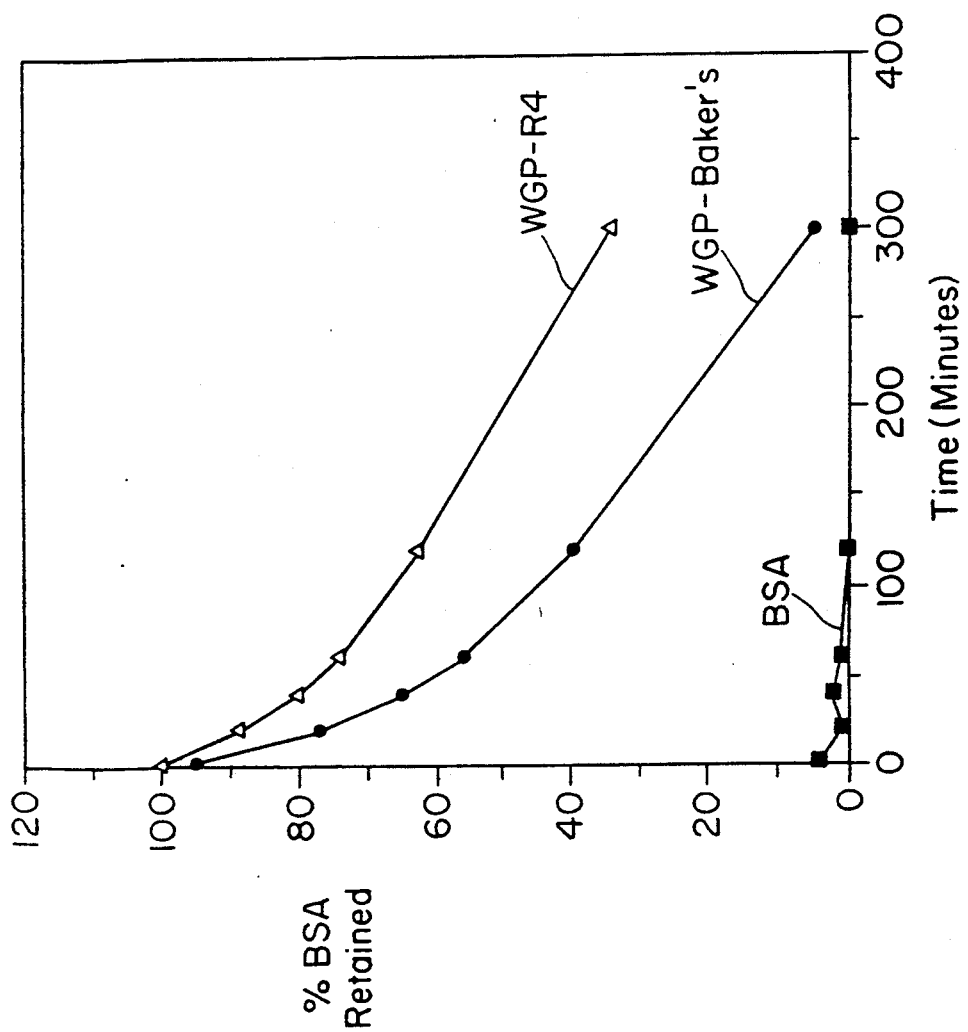
FIG. 2 is a graph illustrating the rate of release of bovine serum albumin (BSA) from whole glucan particles of different permeabilities.

The release mechanism of the drug from the cavity of the whole glucan particles into the physiological environment is through natural diffusion and/or degradation of the polymeric glucan network. The rate of release of the drug can be controlled by changing the ratio of $\beta(1-6):\beta(1-3)$ in the glucan. Methods of modifying and otherwise manipulating the ratio of $\beta(1-6):\beta(1-3)$ linkages, thereby altering the properties of the β-glucan matrix, are described in detail by Jamas et al. in U.S. Pat. No. 4,810,646; and in co-pending patent applications U.S. Ser. No. 07/166,929, now abandoned; U.S. Ser. No. 07/297,752 and U.S. Ser. No. 07/297,982, now a U.S. Pat. No. 4,992,540 issued on 2-12-91 the teachings of which are incorporated herein by reference. For example, by chemical, enzymatic or genetic modification of the ratio of $\beta(1-6):\beta(1-3)$ linkages, the water-holding capacity and permeability of the whole glucan particle can be changed, thereby controlling the rate of release of the drug incorporated therein. The effect of reducing permeability of the β-glucan matrix on the release rate of bovine serum albumin (BSA) is illustrated in FIG. 2. Additionally, the size (e.g., molecular weight) of the drug molecule is important. Larger molecules, such as proteins, will exhibit a slower rate of release in vivo, as illustrated in FIG. 1. Thus, the properties of the glucan carrier can be tailored specifically to the drug of interest.

Figure 3:
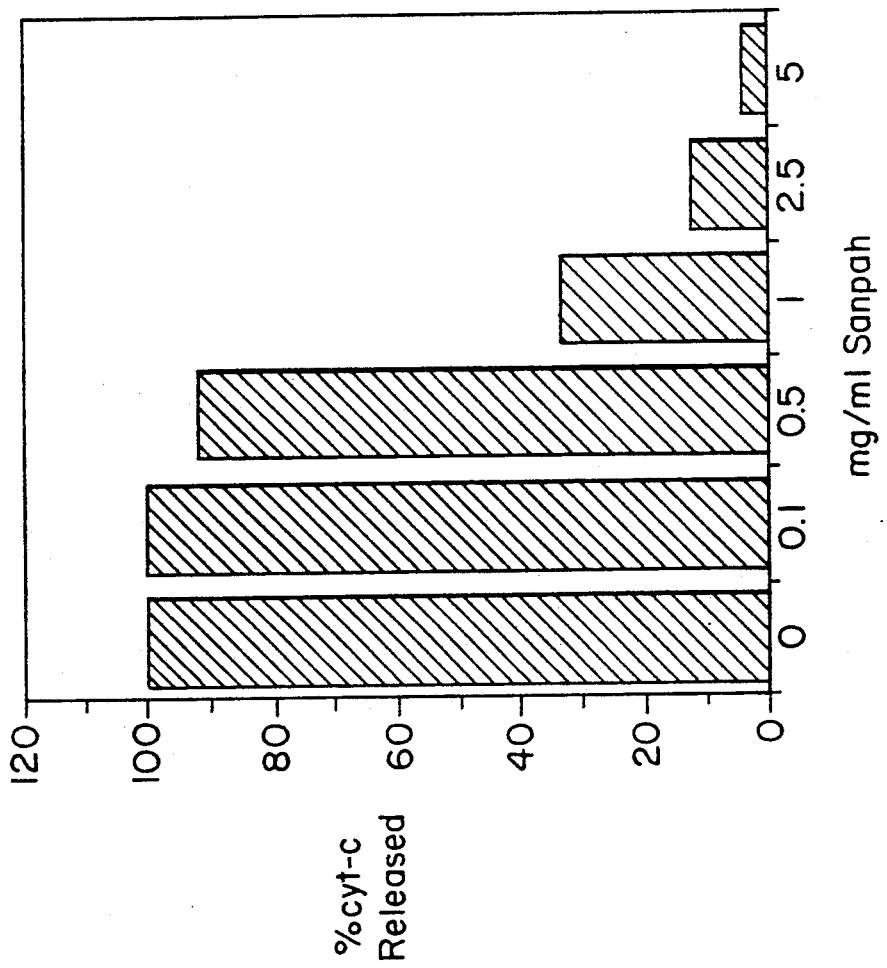
FIG. 3 is a bar graph illustrating the effect on release rate varying amounts of crosslinking of the drug Cytochrome-C with whole glucan particles.

The release rate of a molecule from a whole glucan particle can be modified by crosslinking it to the glucan matrix. This technique is particularly useful for low molecular weight agents which would normally diffuse rapidly through the glucan matrix. This can be achieved, for example, by adding a crosslinking agent to the mixture of β-glucan particles and the drug. The effect of crosslinking is shown in FIG. 3.

The present composition can be administered in any way commensurate with the result or effect desired from the drug. Such methods of administration include orally, intramuscularly, transdermally, intradermally, intravenously, or via the gastrointestinal tract. The composition can be formulated into a liquid solution, tablet, lozenge, suppository, insert or the like. One of the advantages of the present composition is the degradation in vivo of the β-glucan vehicle into non-toxic natural compounds.

The amount of the composition administered to a subject will vary on an individual basis depending upon the drug used, the nature of the treatment or therapy, the type and severity of the symptoms to be treated, the size and physical condition of the individual, and the results sought.

Whole glucan particle compositions have several advantages as immunostimulants compared to alternate materials, such as aluminum hydroxide and glucans prepared by other methods (e.g., Di Luzio et al., *Int. J. Cancer*, 2:773-779 (1979); Manners et al., 1973, *Biochem J*. 135:19-31). Whole glucan particles are more pure than these glucans and retain the in vivo, three dimensional morphology of the yeast cell, thereby providing an intact, hollow structure into which drugs can be incorporated. Glucans prepared by other methods are not intact because the processes used include treatments which disrupt the yeast cell walls, and which destroys the unique functional features of whole glucan particles.

The invention is further illustrated by the following Examples.

EXAMPLE 1

Method to Incorporate Proteins Into Whole Glucan Particles by Swelling and Physical Entrapment Three proteins of different molecular weight were incorporated into whole glucan particles using the following procedure. Solutions of cytochrome-C (cyt. C; Mw=14,000 daltons), bovine serum albumin (BSA; Mw=67,000 daltons) and alcohol dehydrogenase (yeast) (ADH; Mw=150,000 daltons) were dissolved in deionized water at concentrations of approximately 12 mg/ml. One milliliter of each protein solution was added to 150 mg of whole glucan particles (produced from baker's yeast Universal Foods, Wis.) and from *Saccharomyces cerevisiae* R4 according to the method described by Jamas et al. in U.S. Pat. No. 4,810,646 in a test-tube and allowed to swell for two hours at room temperature. The tubes were then transferred to a 45° C. oven and allowed to dry for 12 hours. The resulting dried whole glucan particles contained approximately 80 mg protein/gram of particles.

EXAMPLE 2

Sustained Release of Proteins from Whole Glucan Particles

Three proteins were selected to demonstrate the release rate of different sized molecules from whole glucan particles. Cytochrome-C (Mw=14,000 daltons), BSA (Mw=67,000 daltons) and ADH (Mw=150,000 daltons) were loaded into whole glucan particles according to the method described in Example 1. The dried, loaded particles were resuspended in 10 ml deionized water and were agitated at 37° C. Samples were removed at regular time intervals and assayed spectrophotometrically for released protein. FIG. 1 illustrates the diffusion kinetics of cyt-C. BSA and ADH, from the whole glucan particles, compared to the drugs alone. The amount of time to release 50% of the three drugs is shown in Table 1.

TABLE 1

Time to Release 50% of Protein ($T_{50}$) from Whole Glucan Particles (Derived from Baker's Yeast)

| Protein | Molecular Weight (daltons) | $T_{50}$ (minutes) |
| --- | --- | --- |
| Cytochrome-C | 14,000 | 31 |
| Bovine Serum Albumin | 67,000 | 80 |
| Alcohol Dehydrogenase | 150,000 | 200 |

These results demonstrate that the release rate of the proteins from the whole glucan particles is related to the molecular weight of the protein.

EXAMPLE 3

Control of Release Rate From Whole Glucan Particles by Modifying the Permeability of the Glucan Membrane The following experiment was carried out according to the method described in Example 2, except that whole glucan particles having a higher degree of $\beta(1-6)$ branching compared with other yeast strains were used. These altered whole glucan particles were derived from a mutant strain of yeast, *Saccharomyces cerevisiae* R4 (NRRL Y 15903, described in U.S. Pat. No. 4,810,646). The 435/101, 256 release rate of BSA from whole glucan particles produced from commercial Bakers yeast and the mutant strain R4 according to the procedure described in U.S. Pat. No. 4,810,646, R4 was determined and compared. The results, shown in FIG. 2, demonstrate that the lower permeability of the glucan in particles derived from mutant R4 results in longer retention times of the entrapped BSA ($T_{50}=204$ minutes) compared with particles derived from Bakers yeast ($T_{50}=82$ minutes).

EXAMPLE 4

Control of Release Rate of Small Molecules from Whole Glucan Particles by Chemical Cross-linking Whole glucan particles containing cross-linked cytochrome-C were prepared by first reacting 5 mg cytochrome-C with 2.5 mg of the heterobifunctional cross-linking reagent sulfosuccinimidyl 6-(4'-azido2'-nitrophenylamino) hexanoate (sulfo-SANPAH) in 1 ml 10 mM sodium phosphate buffer pH 7.4 for 16 hours at 25° C. in the dark. One milliliter of the sulfoSANPAH-cytochrome-C conjugate was swelled into the whole glucan particle cavity by mixing with 150 mg of whole glucan particles and incubating at 25° C. for 2 hours in the dark. The sulfo-SANPAH-cytochrome-C conjugate was cross-linked to the whole glucan particles by exposure to bright light. The unreacted sulfo-SANPAH. cytochrome-C and sulfo-SANPAH-cytochrome-C were removed by washing the whole glucan particles in water. The cross-linked whole glucan particle:cytochrome-C conjugate was dried and stored at 4° C.

The release rate of the protein from the particles was determined according to the method described in Example 2. FIG. 3 shows that the release rate of cytochrome-C can be reduced to provide greater than 90% retention over a 24 hour period by increasing the amount of crosslinker added to the whole glucan particles containing cytochrome-C.

EXAMPLE 5

Adjuvant Effect of Whole Glucan Particles in Immunization of Mice With BSA

Figure 4:
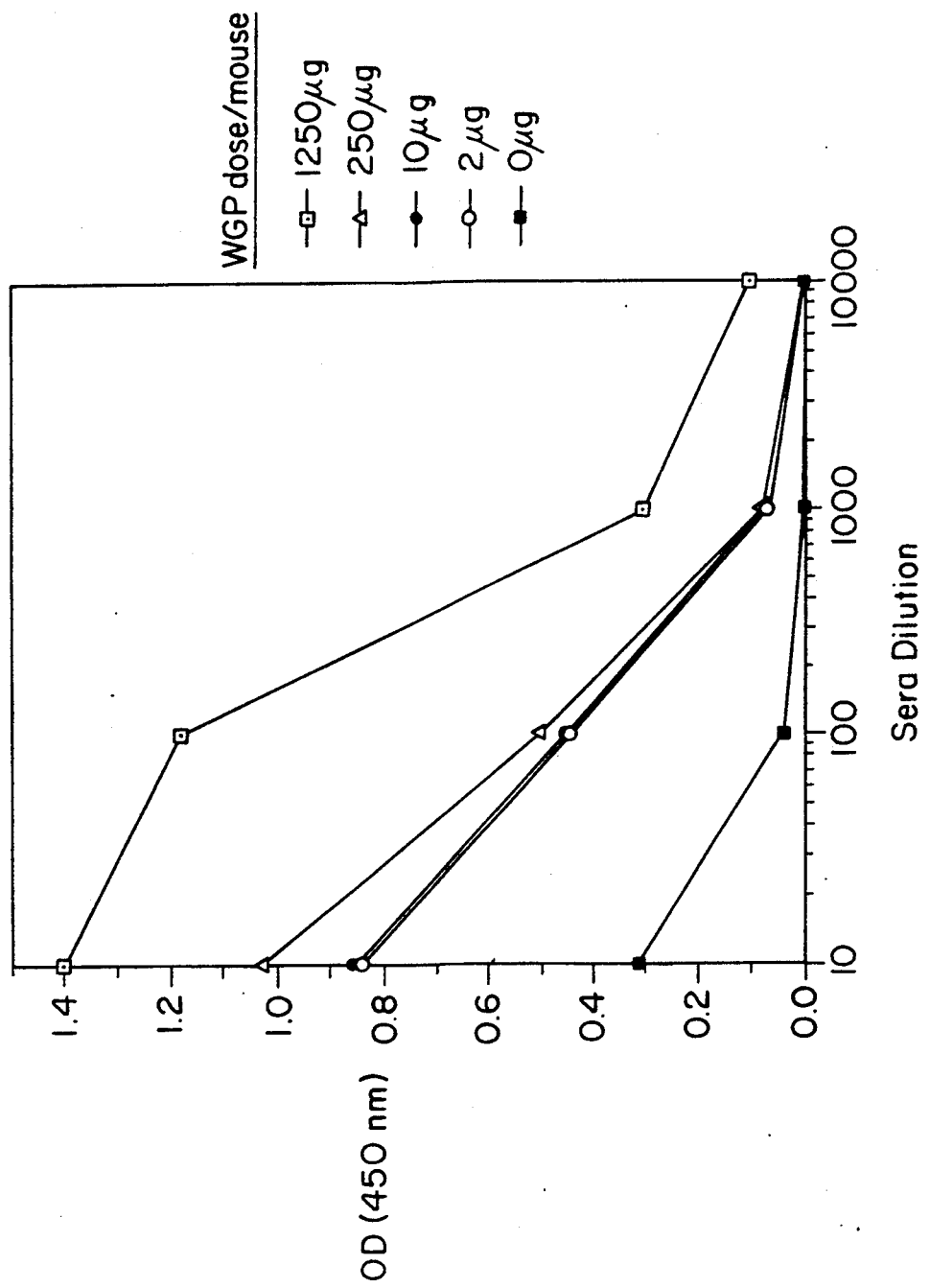
FIG. 4 is a graph illustrating the immunological effect (antibody titer) of whole glucan particles mixed with BSA which were administered to a mouse.
Figure 5:
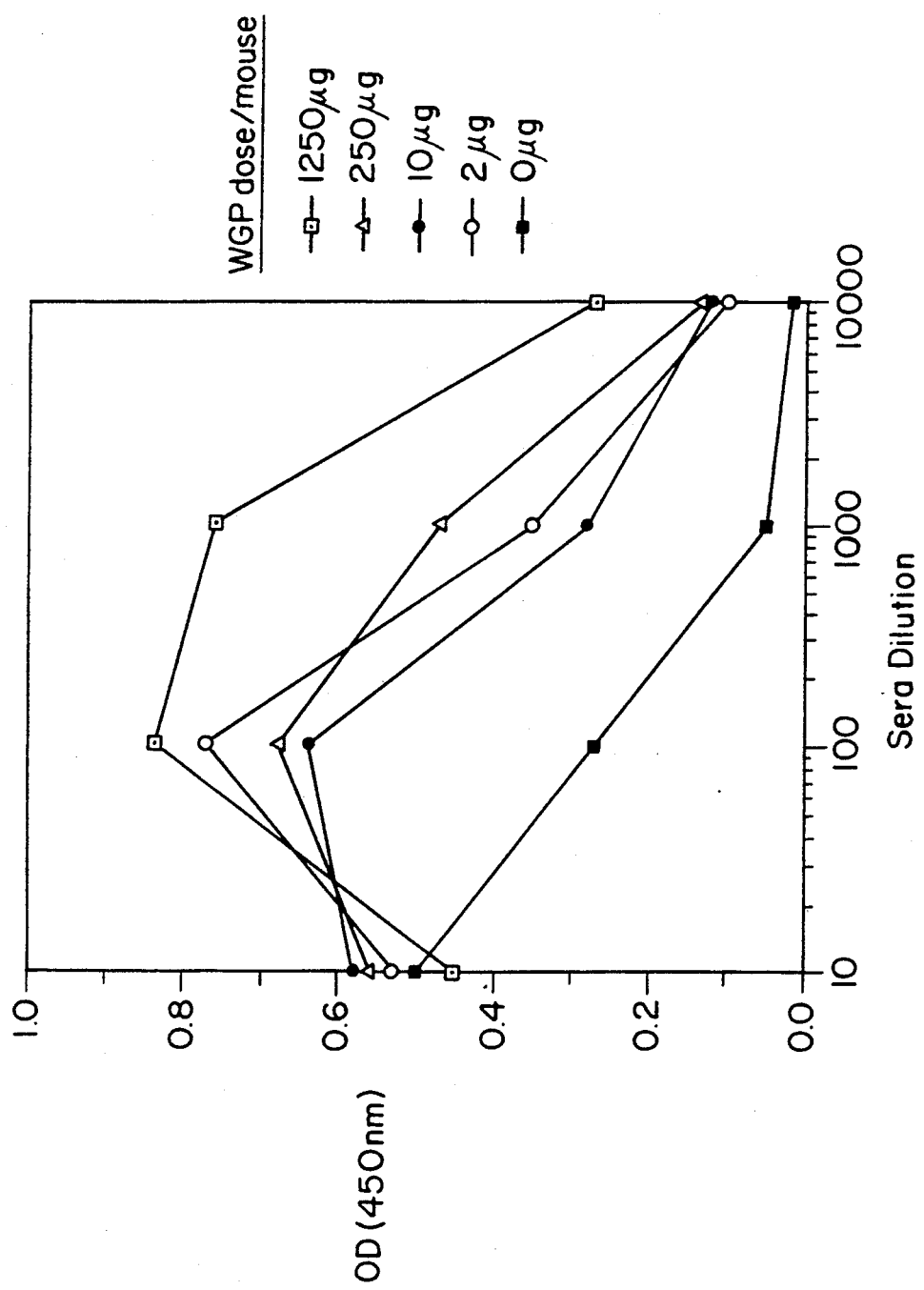
FIG. 5 is a graph illustrating the immunological effect (antibody titer) of whole glucan particles mixed with BSA which were administered as a booster to a mouse.

The in vivo adjuvant effect of whole glucan particles in mice was demonstrated by an increase in antibody production in response to the antigen, BSA. BSA was incorporated into whole glucan particles as described in Example 1. CD-1 mice were immunized intradermally with a range of doses of whole glucan particles mixed with BSA in phosphate buffered saline. The dosages of whole glucan particles, containing 10 μg BSA per mouse, were: 0 μg, 2 μg, 10 μg, 250 μg and 1250 μg. BSA (10 μg) alone was used as a control. Anti-BSA antibody titers were determined by ELISA assay two weeks after immunization. FIG. 4 shows the antibody titers 2 weeks post-immunization. At 3 weeks post-immunization mice were boosted with a second injection of the same dosages, and the antibody titers were determined at two weeks post-boost. FIG. 5 shows the antibody titers 2 weeks post-boost.

The results showed that whole glucan particles had a stimulatory effect on anti-BSA production both in the primary and secondary immune responses (FIGS. 4 and 5) Stimulation was observed at doses as low as 2 μg whole glucan particles per animal (approximately 100 μg/kg body weight).

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A bioerodible pharmaceutical composition for administration to a mammal comprising:
   a. whole glucan particles comprising $\beta(1-6)$ and $\beta(1-3)$ linked glucans; and
   b. a protein;
   wherein said protein is contained within said whole glucan particles, which composition, when placed in a physiological environment, releases the protein over time into the physiological environment and wherein said whole glucan particles bioerode in the physiological environment, which whole glucan particles stimulate a nonspecific immune response in the mammal, thereby providing an adjuvant effect.

2. A pharmaceutical composition of claim 1 wherein the drug comprises a vaccine.

3. A therapeutic composition comprising:
   a. bioerodible whole glucan particles comprising $\beta(1-6)$ and $\beta(1-3)$ linked glucans; and
   b. an antigen or an antigenic determinant
   contained within the whole glucan particles, wherein the antigen or antigen determinant is released from the glucan over time, the glucan particles bioerode in the physiological environment, the wherein the composition stimulates an immune response in the mammal.

4. A method of vaccinating a mammal comprising: administrating to the mammal a composition comprising a vaccine contained within whole glucan particles, whereby the vaccine is continuously released from the whole glucan particle and wherein the whole glucan particle stimulates an immune response in the mammal thereby enhancing the action of the vaccine.

5. A method of claim 1 wherein the composition is administered orally, intramuscularly, transdermally, intradermally, intravenously or through the gastrointestinal tract.

6. A bioerodible pharmaceutical composition for administration to a mammal comprising:
   a. whole glucan particles comprising $\beta(1-6)$ and $\beta(-3)$ linked glucans; and
   b. an antigen or antigenic determinant;

wherein the whole glucan particles are specific for macrophages; wherein the glucan particles are bioeroded within the macrophages thereby activating said macrophages; and wherein the composition releases the antigen or antigenic determinant in or near the macrophages thereby resulting in an enhanced immune response to the antigen or antigenic determinant.

* * * * *

UNITED STATES PATENT AND TRADEMARK OFFICE
CERTIFICATE OF CORRECTION

PATENT NO. : 5,032,401

DATED : July 16, 1991

INVENTOR(S) : Spiros Jamas, Gary R. Ostroff and D. Davidson Easson, Jr.

It is certified that error appears in the above-identified patent and that said Letters Patent is hereby corrected as shown below:

Claim 2, line 52, delete "drug" and insert ---protein---.

Claim 3(b), line 60, before the word "wherein", the word "the" should be deleted.

Claim 6(a), line 9, the term " $\beta(-3)$ " should read --- $\beta(1-3)$ ---.

Signed and Sealed this

Twenty-seventh Day of April, 1993

*Attest:*

MICHAEL K. KIRK

*Attesting Officer*    *Acting Commissioner of Patents and Trademarks*